United States Patent [19]

Lien

[11] 4,443,434
[45] Apr. 17, 1984

[54] ANTIULCER AGENT
[75] Inventor: Eric L. Lien, Paoli, Pa.
[73] Assignee: American Home Products Corporation, New York, N.Y.
[21] Appl. No.: 409,255
[22] Filed: Aug. 18, 1982
[51] Int. Cl.$^3$ ............................................. A61K 37/00
[52] U.S. Cl. .................................................. 424/177
[58] Field of Search .................. 260/112.5 R; 424/177

[56] References Cited

U.S. PATENT DOCUMENTS 4,282,143  8/1981  Sarantakis ....................... 260/112.5

OTHER PUBLICATIONS

Mattes et al., Horm. Metals. Res., 7, 508-511 (1975).
Tyden et al., N. Eng. J. Med., 299, 1466-7 (1978).
Dollinger et al., Horm. Metals. Res., 8, 74-78 (1976).

Primary Examiner—Delbert R. Phillips
Attorney, Agent, or Firm—Richard K. Jackson

[57] ABSTRACT

The octapeptide

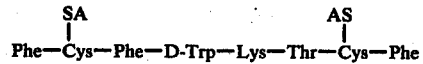

where the A groups are hydrogen or a dithioether bond and salts thereof inhibit gastric and pancreatic secretions and reduce gastrointestinal blood flow in treatment of peptic ulcer disease, acute pancreatitis and Zollinger-Ellison preoperational therapy.

3 Claims, No Drawings

ANTIULCER AGENT

BACKGROUND OF THE INVENTION

Certain analogues of somatostatin (SRIF), like somatostatin itself, inhibit gastric acid secretion. For example, U.S. Pat. No., 4,061,626 discloses the activity of somatostatin, D-Lys$^4$-SRIF and D-Ala$^2$, D-Lys$^4$-SRIF as gastric acid secretion inhibitors as well as inhibitors of growth hormone, glucagon and insulin secretion. Similarly U.S. Pat. No. 4,062,816 indicates that D-Ala$^5$-SRIF inhibits both gastric acid and growth hormone secretion. Inhibition of gastric acid secretion is, however, not a common attribute of all somatostatin analogues. For example, Lippmann et al., Pharmac. Res. Comm., 8 445 (1976) reports that D-Lys$^6$-SRIF had no appreciable effect on gastric acid secretion at a dose as high as 2 μm/kg, s.c. Somatostatin has also been shown to reduce gastrointestinal bleeding. Horm. Metab. Res. 7 508 (1975).

It is known, as reported by Dollinger et al., Horm. Metab. Res. 8 74-78 (1976) that somatostatin reduces bicarbonate concentration slightly but significantly in duodenal aspirate of secretin treated patients and decisively reduces pancreatic enzyme secretion stimulated by pure cholecystokinin-pancreozymin (amylase, chymotrypsin and trypsin). At the same time, insulin secretion was significantly reduced.

The gastro-intestinal hormone gastrin is the most potent stimulant of gastric acid secretion known (1,500 times more potent than histamine on a molar basis). Gastrin is also a powerful stimulant of pancreatic enzyme secretion, being similar to cholecystokinin-pancreozymin in this regard. Zollinger-Ellison syndrome results from the release of large amounts of gastrin from tumors found primarily in the pancreas (these tumors are termed "gastrinomas").

DESCRIPTION OF THE INVENTION

In accordance with this invention there is provided a process for treating peptic ulcer disease which comprises administering to a mammal in need thereof an octapeptide of the formula:

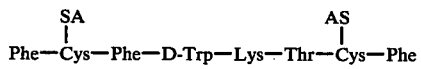

in which the A groups are hydrogen or a direct bond between the two sulfur atoms, or a pharmaceutically acceptable salt or amide thereof, in an amount sufficient to alleviate the symptoms of a peptic ulcer.

The antiulcer agent employed in the method of this invention acts to reduce (1) total gastric volume, (2), hydrogen ion secretion, or (3) hydrogen ion concentration. The reduction of any one of these parameters aids in attenuating the debilitating influence of a peptic ulcer. The use of compounds exhibiting antisecretory activity in the curative and/or prophylactic treatment of peptic ulcer disease is an established, beneficial procedure.

The octapeptide employed in the method of this invention also reduces or stops gastric bleeding in the case of a bleeding ulcer, and inhibits the secretion of pancreatic enzymes thereby simulating physiologic rest in the pancreas which is conventionally achieved in cases of acute pancreatitis by complete withdrawal of oral food and water.

Thus, in accordance with an additional aspect of this invention there is provided a method for treatment of acute pancreatitis which comprises administering an octapeptide of the formula

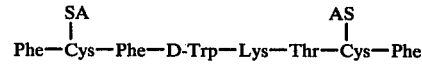

in which the A groups are defined, supra, or a pharmaceutically acceptable salt or amide thereof, to an animal suffering therefrom, in an amount sufficient to inhibit pancreatic enzyme secretion.

The octapeptide employed in the method of this invention is a known compound disclosed in U.S. Pat. No. 4,282,143, the disclosure of which is incorporated herein by reference.

The antiulcer activity of the octapeptide employed in the method of this invention was established with the scientifically recognized, standard test for anti-secretory activity which involves the following procedure in which male Charles River rats weighing 190–260 grams are deprived of food but not water for eighteen hours prior to use. Water is withheld during the actual experiment. The rats are weighed, anesthetized with ether and the pylorus is ligated according to the method of Shay et al., Gastroenterology, 26, 906–913 (1954). Treatment or vehicle control is then administered subcutaneously (s.c.). The rats are housed two per cage and sacrificed with CO$_2$ four hours after ligation. The stomachs are removed, rinsed, and contents emptied into a graduated centrifuge tube. The tubes are centrifuged for twenty minutes at two thousand revolutions per minute and the volume of gastric juice is recorded. Any sample which is obviously contaminated with feces, food or blood is eliminated. An aliquot of each sample is frozen for later analysis of pepsin. The pH is measured and one milliliter of gastric juice is titrated with 0.1 N NaOH to a pH of 7.0–7.4. The data are analyzed by analysis of variance and, using the pooled error variance, t-comparisons are made between the groups. The results obtained demonstrated 67 percent inhibition of total acid output at 1 mg/kg s.c., 89 percent inhibition of total acid output at 2 mg/kg s.c. and 83 percent inhibition of total acid output at 4 mg/kg s.c.

The effect of the octapeptide on gastric blood flow was established by the following procedure:

Rats weighing 280–350 gms were used. Rats were anesthatized with 50 mg/kg Nembutal and their left jugular veins cannulated. Somatostatin, 1 mg/kg/hr, was infused i.v. in one group of rats while a second group received a saline infusion. In a second experiment the octapeptide of the method of this invention, 1 mg/kg, or saline was injected s.c. Thirty minutes following the start of the experiment 20 μCi/rat of $^{86}$RbCl was injected i.v. The rats were killed 20 seconds later by injection of 0.5 ml Nembutal. The blood flow to the stomach was determined by counting $^{86}$Rb in the disected stomachs of the rats.

| Drug | % total $^{86}$Rb$^a$ in stomach |
|---|---|
| saline | 1.20 ± 0.05 |
| somatostain | 1.03 ± 0.05+ |
| saline | 1.36 ± 0.12 |

| Drug | % total $^{86}Rb^a$ in stomach |
|---|---|
| octapeptide | 0.96 ± 0.04* |

$^a$Mean ± S.E.M., 5 animals per group
$^+$p < 0.05;
*p < 0.01

From this comparative study it can be seen that the octapeptide reduces gastro-intestinal blood flow comparably to somatostatin, thereby establishing its value in treating gastro-intestinal bleeding attending peptic ulcer disease.

The effect of the octapeptide used in the method of this invention on the exocrine function of the pancreas was established by the following procedure:

Streptozotocin diabetic dogs were fasted and insulin withdrawn for 18 hours. The dogs received a s.c. injection of saline or the octapeptide employed in the method of this invention (100 μg/kg) followed immediately by oral administration of a commercial triglyceride suspension (Lipomal, 5 mg/kg). Plasma samples were obtained at regular intervals and assayed for triglycerides.

| Time (hrs) | Triglyceride Levels (mg/dl)$^a$ | |
|---|---|---|
| | Saline | Octapeptide |
| 0 | 56 ± 10 | 57 ± 10 2 |
| 1 | 114 ± 32 | 36 ± 2$^+$ |
| 2 | 324 ± 106 | 37 ± 1 |
| 3 | 354 ± 132 | 34 ± 2$^+$ |
| 4 | 226 ± 86 | 47 ± 10 |

$^a$Mean ± S.E M., 3 dogs/group
$^+$p < 0.05

From this study it can be seen that substantially no fat was absorbed by the test animals being treated with the octapeptide, indicating physiologic rest of the pancreas with suppressed bile flow and/or decreased exocrine pancreatic function.

As a result of these properties, the polypeptide employed in this invention is useful in the treatment of patients suffering from peptic ulcer disease, pancreatitis and Zollinger-Ellison syndrome in that the octapeptide reduces gastric acid secretion, gastric blood flow and pancreatic enzyme release. The combined actions of the octapeptide are especially valuable in early treatment of Zollinger-Ellison syndrome to stabilize the patient during preoperational diagnoses and procedures for locating of the tumor(s).

For each indication, the octapeptide is parenterally (i.v., i.m., s.c., etc.) administered either neat or as a composition. Suitable liquid compositions include sterile solutions for parenteral administration. The polypeptide may be employed alone as the sole basis for treatment or it may be advantageously employed in conjunction with a treatment regimen utilizing a conventional antacid such as calcium carbonate, magnesium carbonate, bismuth carbonate, aluminum or magnesium hydrated oxides, magnesium glycinate, magnesium trisilicate, calcium trisilicate, or sodium bicarbonate to maintain gastric acidity from about a pH of 3 to 5 or higher. Likewise, the octapeptide may be used in conjunction with known anticholingergic agents or known $H_2$-receptor blocking agents.

The pharmaceutical compositions containing the anti-secretory agent of this invention are formulated conventionally with a sterile liquid carrier. Unit dosage forms containing from about 0.05 to 50 milligrams of polypeptide are especially suitable.

As with any gastro-intestinal disease treatment, the dosage and treatment regimen employing an anti-secretory agent is entirely subjective and must be regulated by the physician to the individual patients need subject to such variables as age, severity of the condition, mode of administration, companion medication, response to the treatment, etc. Therefore, the dose of polypeptide to be employed in any given case must be determined by the attending physician.

The use of the specific octapeptide employed in the method of this invention, because of its potency, avoids the necessity for administration by infusion which is characteristic of somatostatin therapy. In addition, the method of this invention, because of the selectivity of action of the octapeptide employed, avoids the problem attending the use of somatostatin of significant reduction in blood serum levels of insulin and glucagon which requires adjunct insulin therapy.

What is claimed is:

1. A method for treating peptic ulcer disease which comprises administering to a mammal in need thereof an octapeptide of the formula:

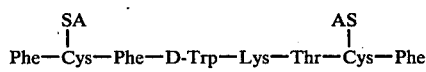

in which the A groups are hydrogen or a direct bond between the two sulfur atoms, or a pharmaceutically acceptable salt or amide thereof, in an amount sufficient to alleviate the symptoms of a peptic ulcer.

2. A method for treating acute pancreatitis which comprises administering an octapeptide of the formula:

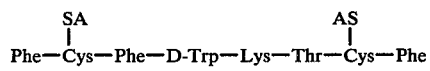

in which the A groups represent hydrogen or a direct dithioether bond, or a pharmaceutically acceptable salt or amide thereof, to a mammal suffering therefrom in an amount sufficient to inhibit pancreatic enzyme secretion.

3. A method for stabilizing a mammal suffering from Zollinger-Ellison syndrome during preoperational diagnosis and tumor location which comprises administering an octapeptide of the formula:

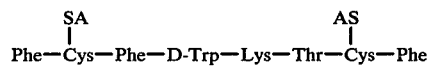

in which the A groups represent hydrogen or a direct dithioether bond, or a pharmaceutically acceptable salt or amide thereof, to said mammal in an amount sufficient to inhibit pancreatic gastrin secretion.

* * * * *